US012759007B2

(12) United States Patent
Zou et al.

(10) Patent No.: US 12,759,007 B2
(45) Date of Patent: Oct. 13, 2026

(54) MULTI-PURPOSE AROMA DIFFUSER

(71) Applicant: SHENZHEN JINGXINTAI HOUSEWARE CO., LTD., Shenzhen (CN)

(72) Inventors: Jinshan Zou, Shenzhen (CN); Xianshun Deng, Shenzhen (CN); Shouyong Zheng, Shenzhen (CN)

(73) Assignee: SHENZHEN JINGXINTAI HOUSEWARE CO., LTD., Shenzhen (CN)

( * ) Notice: Subject to any disclaimer, the term of this patent is extended or adjusted under 35 U.S.C. 154(b) by 376 days.

(21) Appl. No.: 18/501,809

(22) Filed: Nov. 3, 2023

(65) Prior Publication Data

US 2025/0083173 A1 Mar. 13, 2025

(30) Foreign Application Priority Data

Sep. 13, 2023 (CN) ......................... 202322489243.3

(51) Int. Cl.

*B05B 15/625* (2018.01)
*A61L 9/04* (2006.01)
*B05B 7/24* (2006.01)

(52) U.S. Cl.

CPC .............. *B05B 15/625* (2018.02); *A61L 9/04* (2013.01); *B05B 7/24* (2013.01)

(58) Field of Classification Search

CPC ................................... A61L 9/04; B05B 7/24
See application file for complete search history.

(56) References Cited

U.S. PATENT DOCUMENTS

2012/0251296 A1* 10/2012 Jorgensen ........... B05B 17/0607 415/116

* cited by examiner

*Primary Examiner* — Kevin Joyner
(74) *Attorney, Agent, or Firm* — MUNCY, GEISSLER, OLDS & LOWE, P.C.

(57) ABSTRACT

A multi-purpose aroma diffuser, comprising an aroma diffuser body mechanism and a base mechanism, wherein the aroma diffuser body mechanism atomizes aromatherapy essential oils into mist and diffuse the mist into air, the base mechanism is suitable for being placed on a floor, while the aroma diffuser body mechanism is suitable for being placed on a tabletop; and the aroma diffuser body mechanism is also suitable for being detachably connected to the base mechanism, so that the aroma diffuser body mechanism is supported by the base mechanism. The present invention solves the problem of how to provide a multi-functional and multi-purpose aroma diffuser suitable for use in various scenarios; and the multi-purpose aroma diffuser of the present invention is suitable for use in various scenarios such as homes, offices and shops, and lighting/ambient light functions are added, so the multi-purpose aroma diffuser of the present invention achieves more practical functions.

8 Claims, 9 Drawing Sheets

MULTI-PURPOSE AROMA DIFFUSER

TECHNICAL FIELD

The present invention relates to the field of environmental electrical appliances, in particular to a multi-purpose aroma diffuser.

BACKGROUND TECHNOLOGY

Aromatherapy not only brings fragrance to the environment but also has health benefits such as relaxation, fatigue reduction, and mood enhancement. An aroma diffuser can atomize liquid essential oils into mist. The mist of essential oils floats in the air and gradually disperses into the environment, filling the entire space. With the improvement of living standards, more and more places like homes, offices, and shops are equipped with aroma diffusers.

The current aroma diffusers in the prior art are mostly designed to be placed on tabletops, shelves, or bedside tables. Some can be plugged into power outlets, while others are suitable for use in cars. However, there is currently no fragrance diffuser that can be directly placed on the floor in the prior art.

Furthermore, most of the existing aroma diffusers only have the function of dispersing fragrance, making them limited in functionality and appearance, which may not suit modern homes, offices, shops and other places.

In summary, there is an urgent need to address the challenge of providing a multi-functional and multi-purpose aroma diffuser that can be used in various settings.

SUMMARY OF THE INVENTION

The present invention aims to provide a multi-purpose fragrance diffuser, which is suitable for use in various scenarios and is equipped with lighting/ambience lighting functions.

In order to achieve above purpose, the present invention offers following technical solutions: a multi-purpose aroma diffuser, comprises an aroma diffuser body mechanism and a base mechanism, wherein the aroma diffuser body mechanism atomizes aromatherapy essential oils into mist and diffuses the mist into air, the base mechanism is suitable for being placed on a floor, the aroma diffuser body mechanism is suitable for being placed on a tabletop, and the aroma diffuser body mechanism is suitable for being detachably connected to the base mechanism, so that the aroma diffuser body mechanism is supported by the base mechanism.

In the multi-purpose aroma diffuser mentioned of above technical solutions, the aroma diffuser body mechanism comprises at least one part which is capable of radiating illumination light/ambient light outwards.

In the multi-purpose aroma diffuser of above technical solutions, the aroma diffuser body mechanism comprises a shell assembly, an atomization assembly, a main circuit board, batteries and an air pump; the shell assembly comprises a bottom shell, an outer upper shell connected to upper portions of the bottom shell, an inner upper shell embedded and fixed in the outer upper shell, a light guide bracket connected below the bottom shell, and a base fitting plate embedded in the light guide bracket; the main circuit board is fixed in an inner layer of the light guide bracket of the shell assembly, on the main circuit board are respectively provided a first charging interface and lamp beads, the first charging interface penetrates from the bottom shell of the shell assembly, and an emitting surface of the lamp beads faces the light guide bracket of the shell assembly; both the batteries and the air pump are accommodated and fixed in the shell assembly, and are in electrical connection with the main circuit board respectively; the atomization assembly is detachably connected and embedded in the inner upper shell, the air pump is configured to provide an air source for the atomization assembly, so that the atomization assembly atomizes aromatherapy essential oils into mist and diffuses the mist into air; and the base fitting plate of the shell assembly is adapted to be detachably connected to the base mechanism.

In the multi-purpose aroma diffuser of above technical solutions, the atomization assembly comprises a main atomization shell, a jet tube, an atomization head, an essential oil tube, a mist outlet upper cover assembly and an essential oil bottle; the essential bottle is connected to a lower end of the main atomization shell, an air inlet pipe is formed in the main atomization shell, the air inlet pipe forms an air inlet on a surface of the main atomization shell, and an air outlet of the air inlet pipe is arranged at the lower end of the main atomization shell and faces the essential oil bottle, a first mist outlet is also formed in the main atomization shell, and the first mist outlet communicates with the essential oil bottle and an upper cavity of the main atomization shell; the atomization head is provided with an atomization nozzle and an essential oil tube connection portion, and the essential oil tube is connected to the essential oil tube connection portion of the atomization head; an air inlet end of the jet tube is plugged into the air outlet of the air inlet pipe, and an air outlet end of the jet tube and the atomization head are plugged and fixed to each other, so that the air outlet end of the jet tube is aligned with the atomization nozzle of the atomization head, and the essential oil tube is inserted into the essential oil bottle; on the mist outlet cover assembly forms a second mist outlet, and the mist outlet cover assembly is embedded and fixed in an upper cavity of the main atomization shell; and the air inlet pipe of the main atomization shell allows for passage of airflow, when airflow passes through the air inlet pipe and is ejected from the jet tube, a Venturi effect forms near the atomization nozzle of the atomization head, so that the atomization head absorbs aromatherapy essential oils from the essential oil bottle through the essential oil tube, and the aromatherapy essential oils are atomized into mist at the atomization nozzle of the atomization head, and the mist passes through the first mist outlet of the main atomization shell and the second mist outlet of the mist outlet upper cover assembly in sequence and is diffused into air.

In the multi-purpose aroma diffuser of above technical solutions, inside the mist outlet upper cover assembly is provided a porous plate.

In the multi-purpose aroma diffuser of above technical solutions, the inner upper shell is provided with an air inlet interface and an air outlet of the air pump is communicated to the air inlet interface of the inner upper shall; when the atomization assembly is connected and embedded in the inner upper shell, the inner upper shell is sealed; and when the air pump runs, airflow is poured into the sealed inner upper shell from the air inlet interface, and the airflow sealed in the inner upper shell is forced to pass through the air inlet on the surface of the main atomization shell and enters into the air inlet pipe.

In the multi-purpose aroma diffuser of above technical solutions, inside the inner upper shell is provided a guide plate having a notch.

In the multi-purpose aroma diffuser of above technical solutions, the base mechanism comprises a base assembly, a support rod assembly, and a rotary connection assembly from bottom to top; and the base fitting plate of the shell assembly of the aroma diffuser body mechanism is adapted to be detachably connected to the rotary connection assembly of the base mechanism.

In the multi-purpose aroma diffuser of above technical solutions, the base assembly comprises a main base plate and a base power supply assembly; the base power supply assembly comprises a first box body and a power supply circuit board, on the first box body forms a first slot, the first box body is fixed on the main base plate, the power supply circuit board is accommodated in the first box body, the power supply circuit board is respectively equipped with a second charging interface and power supply rings, the second charging interface penetrates the first box body, and the power supply rings also pass the first slot; and the support rod assembly comprises a support tube body, ends of the support tube body are embedded with end shells, and inside the end shells are accommodated transfer circuit boards, the transfer circuit boards are equipped with first conductive pillars, the first conductive pillars penetrate surfaces of the end shells, and the transfer circuit boards at the ends of the support tube body are connected through wires; the rotary connection assembly comprises a second box body and rotary connection circuit boards, on the second box body forms a second slot, the rotary connection circuit boards are accommodated in the second box body, the rotary connection circuit boards are respectively equipped with second electricity receiving rings and second conductive pillars, the second conductive pillars penetrate the second box body, the second electricity receiving rings also pass the second slot of the second box body; when either end of the support rod assembly is plugged into the first slot of the base assembly, the first conductive pillars of the support rod assembly are in contact with the power supply rings of the base assembly; when either end of the support rod assembly is plugged into the second slot of the base assembly, the first conductive pillars of the support rod assembly are in contact with the second electricity receiving rings of the rotary connection assembly; on the base fitting plate of the aroma diffuser body mechanism forms a base fitting slot, the main circuit board of the aroma diffuser body mechanism is further equipped with a first electricity receiving rings, and the first electricity receiving rings penetrate the base fitting slot of the base fitting plate; when the rotary connection assembly of the base mechanism is inserted into the base fitting slot of the aroma diffuser body mechanism, the second conductive pillars of the base mechanism are in contact with the first electricity receiving rings of the aroma diffuser body mechanism.

In the multi-purpose aroma diffuser of above technical solutions, inside the base fitting plate of the aroma diffuser body mechanism is provided a first permanent magnet; inside the rotary connection assembly of the base mechanism is provided a second permanent magnet; and when the rotary connection assembly of the base mechanism is inserted into the base fitting slot of the aroma diffuser body mechanism, the first permanent magnet and the second permanent magnet are attracted together.

Compared to the prior art, the present invention has following beneficial effects: the multi-purpose aroma diffuser in the present invention comprises an aroma diffuser body mechanism which can be placed on a tabletop individually or used in conjunction with a base mechanism to stand on the floor, which enables the multi-purpose aroma diffuser to be suitable for various settings, including homes, offices, and shops. Additionally, the present invention incorporates lighting/ambient light functions, thereby further enhancing practicality and functionality thereof.

Figure 1:
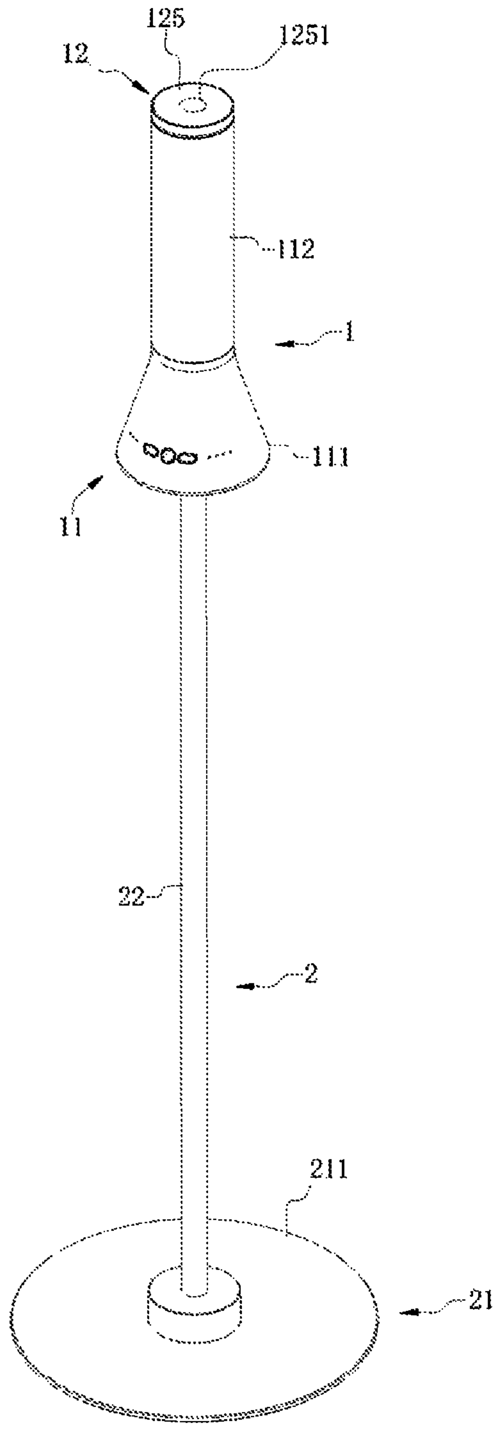
FIG. 1 is a perspective view of the present invention.

The markups in the drawings are indicated as follows:

1—diffuser body mechanism;
11—shell assembly;
111—bottom shell;
112—outer upper shell;
113—inner upper shell;
1131—air inlet interface;
114—air pump bracket;
115—light guide bracket;
116—base fitting plate;
1161—base fitting slot;
117—guide plate;
1171—notch;
12—atomization assembly;
121—main atomization shell;
1211—air inlet pipe;
1212—first mist outlet;
122—jet tube;
123—atomization head;
1231—atomization cavity;
1232—atomization nozzle;
1233—essential oil tube connection portion;
124—essential oil tube;
125—mist discharge upper cover assembly;
1251—second mist outlet;
1252—porous plate;
126—essential oil bottle;
13—main circuit board;
131—first electricity receiving ring;
132—lamp bead;
133—first charging interface;
14—battery;
15—air pump;
16—first permanent magnet;
2—base mechanism;
21—base assembly;
211—main baseboard;
212—base power supply assembly;
2121—first box body;
2122—power supply circuit board;
2123—second charging interface;
2124—power supply ring;
2125—first slot;
22—support assembly;
221—support tube body;
222—end shell;
223—transfer circuit board;

2231—first conductive pillar;
224—wire;
23—rotary connection assembly;
231—second box body;
2311—second slot;
232—rotary connection circuit board;
2321—second electricity receiving ring;
2322—second conductive pillar; and
233—second permanent magnet.

Specific Embodiments

The technical solutions in the embodiments of the present invention will be clearly and completely described below with reference to the accompanying drawings in the embodiments of the present invention. It is obvious that the described embodiments are only some rather than all of the embodiments of the present invention. Based on the embodiments of the present invention, all other embodiments obtained by those of ordinary skill in the art without creative efforts shall fall within protection scope of the present invention.

An embodiment of the present invention provides a multi-purpose aroma diffuser capable of atomizing essential oils into mist and diffusing the mist into air.

Figure 2:
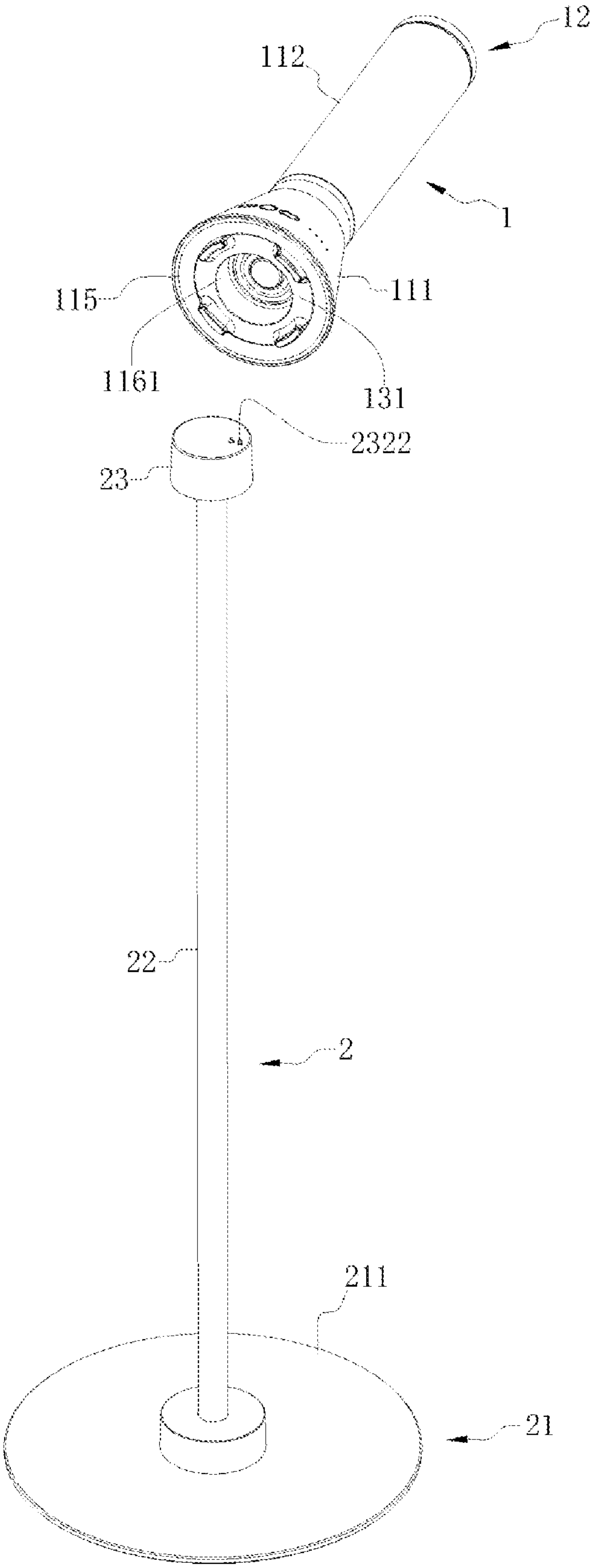
FIG. 2 is a schematic diagram of a separation/combination process of an aroma diffuser body mechanism and a base mechanism in the present invention.

Please refer to FIG. 1 and FIG. 2, the multi-purpose aroma diffuser of the present embodiment comprises an aroma diffuser body mechanism 1 and a base mechanism 2, wherein the aroma diffuser body mechanism 1 serves as a functional unit, used to atomize aromatherapy essential oils into mist and diffuse the mist into air, and undertakes other practical functions, and the base mechanism 2 serves as a support unit, used to support the aroma diffuser body mechanism 1.

The aroma diffuser body mechanism 1 atomizes aromatherapy essential oils into mist and diffuses the mist into air.

The base mechanism 2 is suitable for being placed on a floor.

The aroma diffuser body mechanism 1 is suitable for being placed on a tabletop, and the aroma diffuser body mechanism 1 is also suitable for being detachably connected to the base mechanism 2, so that the aroma diffuser body mechanism 1 is supported by the base mechanism 2.

Further, the aroma diffuser body mechanism 1 comprises at least one part which is capable of radiating illumination light/ambient light outwards, so that the multi-purpose aroma diffuser of the present embodiment has lighting/ambient light functions.

Figure 3:
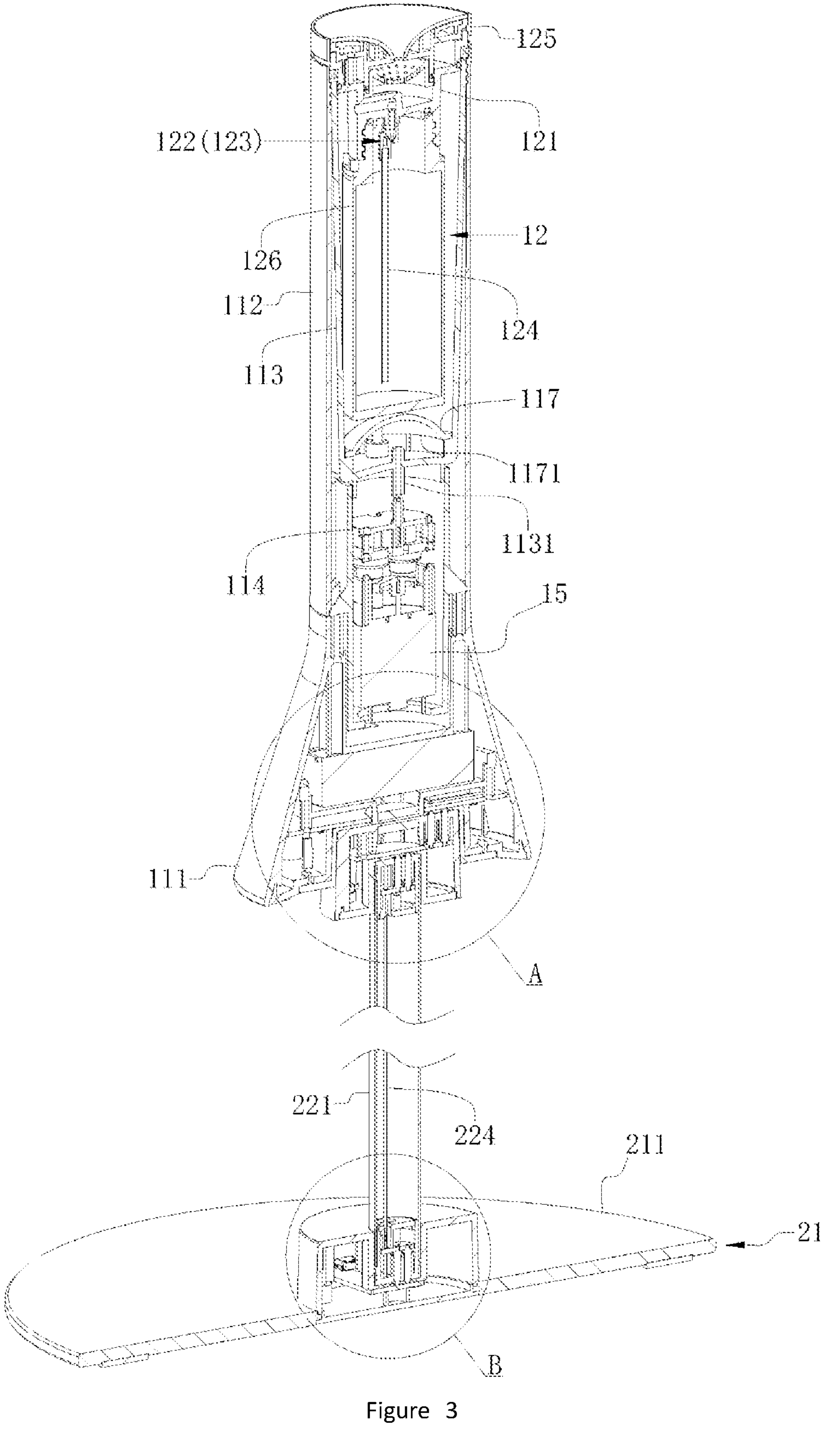
FIG. 3 is a cross-sectional structural view of the present invention.
Figure 4:
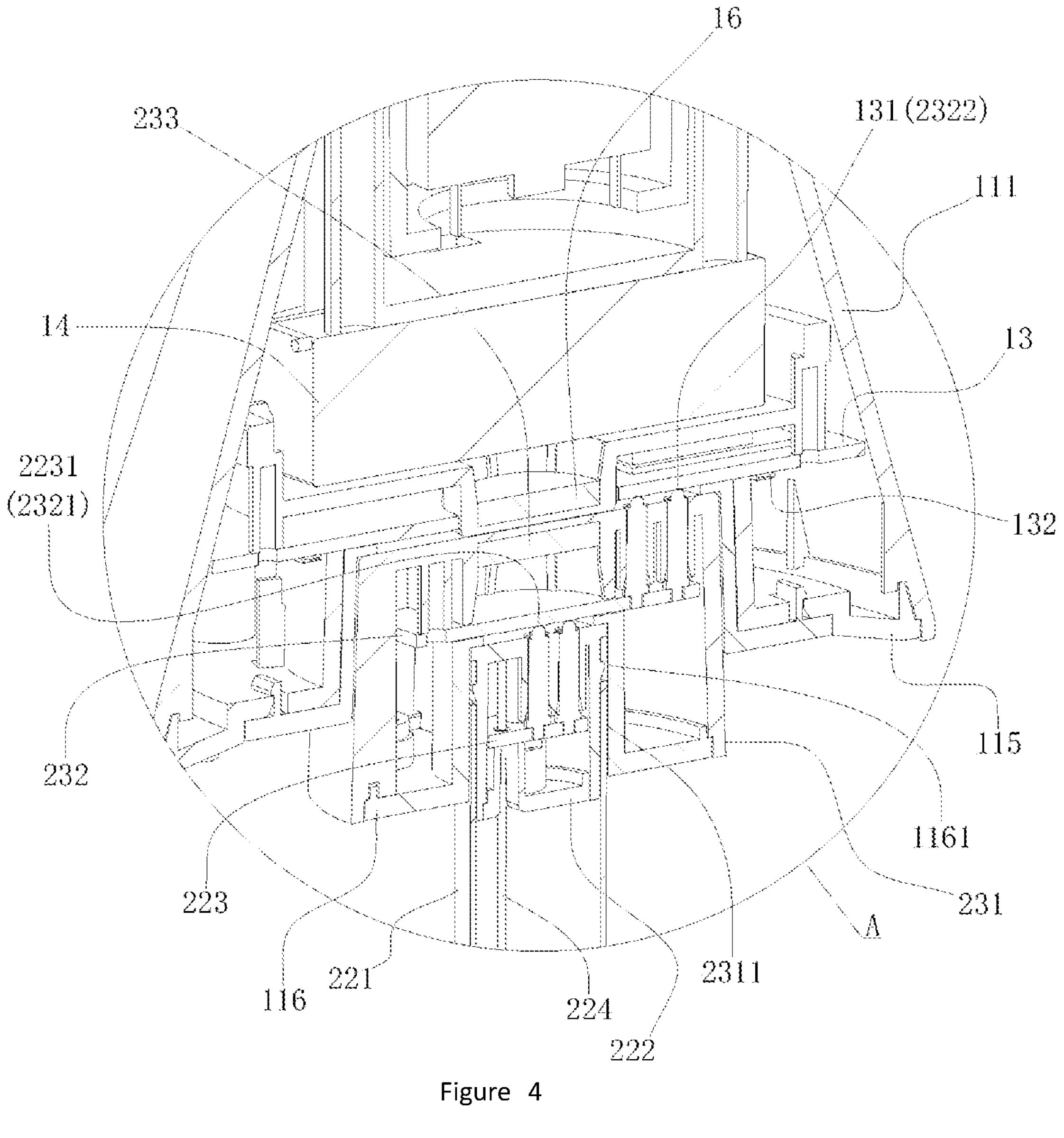
FIG. 4 is an enlarged view of a part "A" in FIG. 3.
Figure 5:
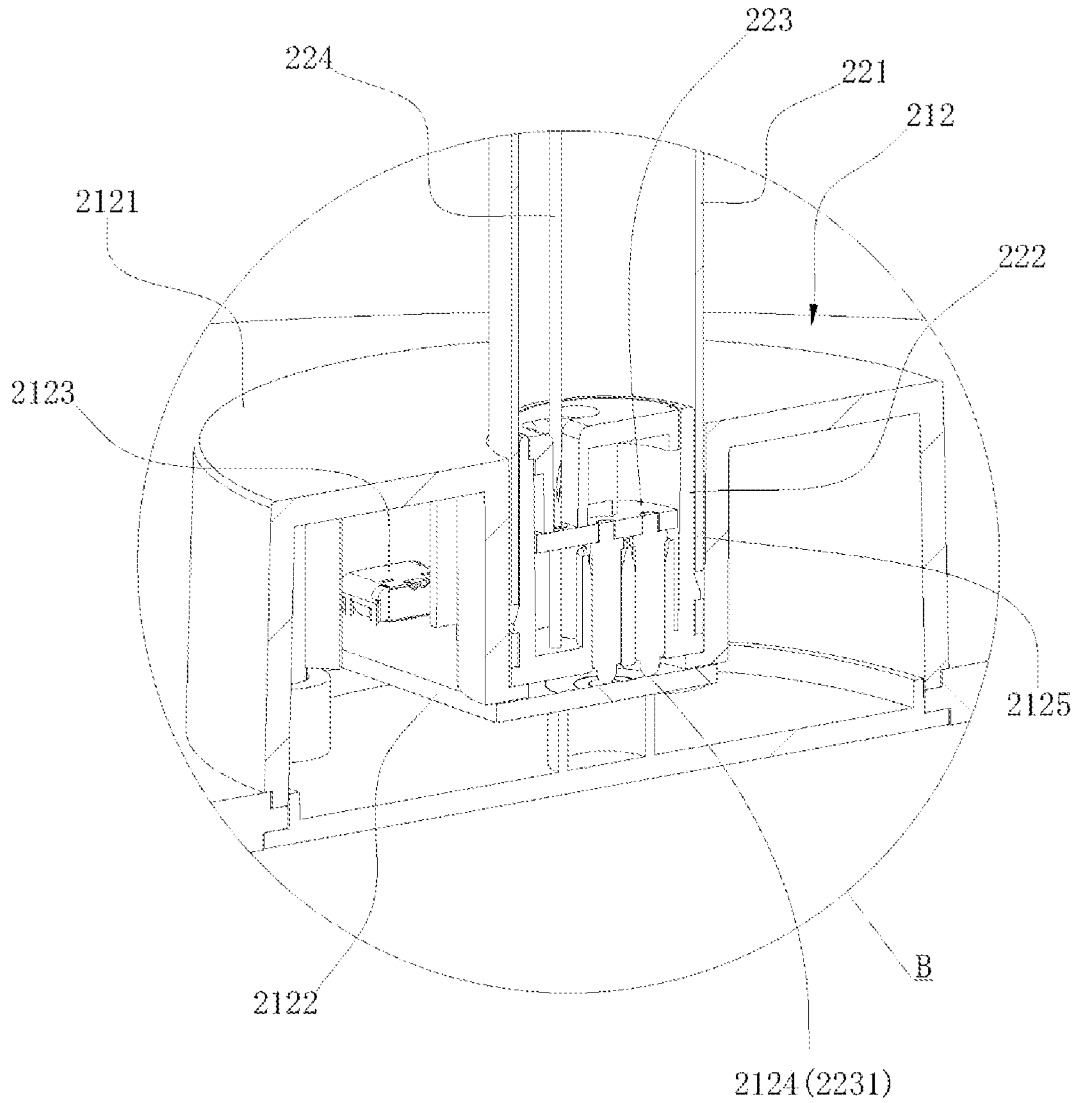
FIG. 5 is an enlarged view of a part "B" in FIG. 3.
Figure 6:
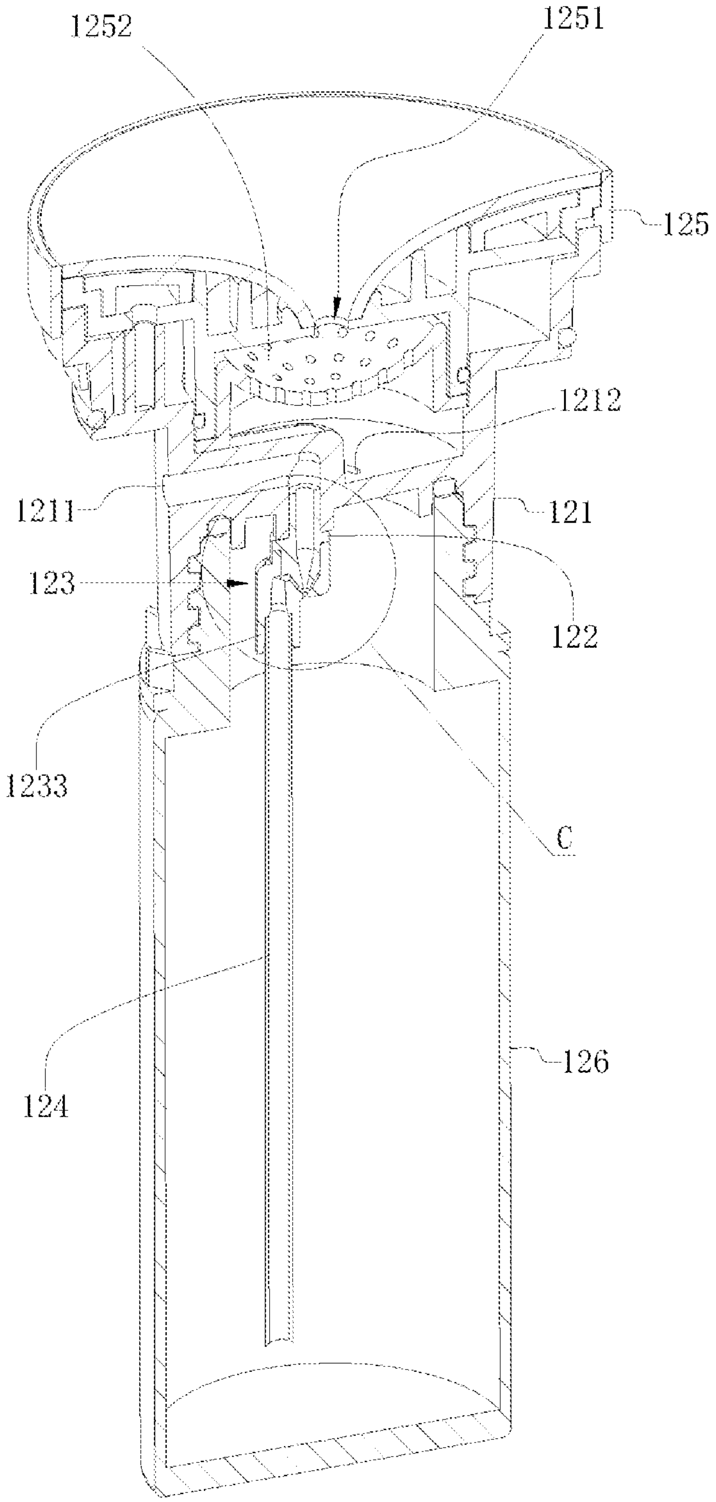
FIG. 6 is a structural view of an atomization assembly of the present invention.
Figure 7:
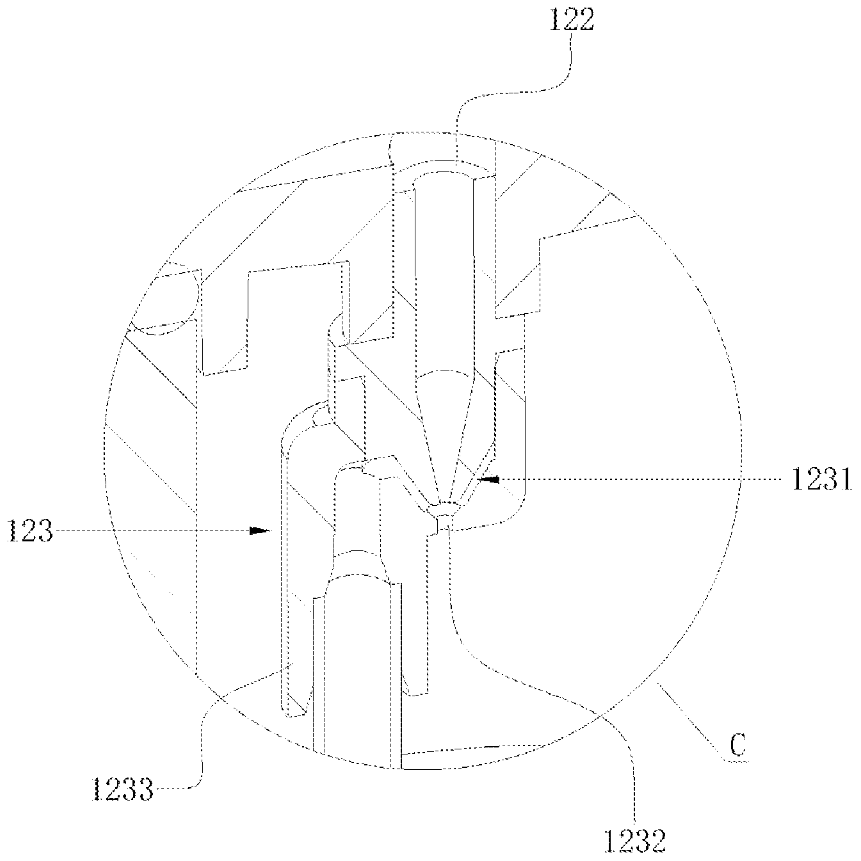
FIG. 7 is an enlarged view of a part "C" in FIG. 6.

Please refer to FIG. 3 and FIG. 4, the aroma diffuser body mechanism 1 comprises a shell assembly 11, an atomization assembly 12, a main circuit board 13, batteries 14 and an air pump 15, wherein the main circuit board 13 is a printed circuit board (PCB), which is equipped with an MCU such as a microcontroller as a main control, the batteries 14 are rechargeable lithium batteries such as two 18650 batteries or customized lithium battery blocks, and the air pump 15 is a small DC motor-driven air pump capable of providing airflow.

The shell assembly 11 comprises a bottom shell 111, an outer upper shell 112 connected to upper portions of the bottom shell 111, an inner upper shell 113 embedded and fixed in the outer upper shell 112, a light guide bracket 115 connected below the bottom shell 111, and a base fitting plate 116 embedded in the light guide bracket, in the present embodiment, the bottom shell 111 is a truncated cone-shaped shell made of engineering plastic or metal materials, the outer upper shell 112 and the inner upper shell 113 are both cylindrical shells made of engineering plastic or metal materials, the bottom shell 111, the outer upper shell 112 and the inner upper shell 113 are respectively connected to each other through screws or buckles, the light guide bracket 115 comprises an engineering plastic base plate with a transparent, translucent or frosted effect, which is fixed to lower portions of the bottom shell 111 through screws, and the base fitting plate 116 is an engineering plastic or metal base plate with an opaque, transparent, translucent or frosted effect, and is buckled and embedded in the light guide bracket 115.

The main circuit board 13 is fixed in an inner layer of the light guide bracket 115 of the shell assembly 11, in the present embodiment, the main circuit board 13 is fixed with screws and hung on a position where the bottom shell 111 locates, and when the light guide bracket 115 is fixed, the main circuit board 13 is covered; on the main circuit board 13 are respectively provided a first charging interface 133 and lamp beads 132, wherein the first charging interface 133 is one of Type-C interface, Micro USB interface and Mini USB interface, which is mounted on the main circuit board 13 by plug-in; and the lamp beads 132 are LED lamp beads, which are mounted on the main circuit board 13 in a form of patches. In the present embodiment, a plurality of the lamp beads 132 are arranged in a ring shape on a surface of the main circuit board 13; the first charging interface 133 penetrates from the bottom shell 111 of the shell assembly 11, and an emitting surface of the lamp beads 132 faces the light guide bracket 115 of the shell assembly 11, so that light of the lamp bead 132 can pass through the light guide bracket 115 of the shell assembly 11 and radiate outward, thereby realizing functions of radiating lighting/ambience lighting outwards.

Both the batteries 14 and the air pump 15 are accommodated and fixed in the shell assembly 11, and are in electrical connection with the main circuit board 13 respectively, and in the present embodiment, the batteries are fixed in the bottom shell 11 through adhesives or brackets, and the air pump 15 is fixed inside a position where the bottom shell 111 and the outer upper shell 112 connects through an air pump bracket 114.

The atomization assembly 12 is detachably connected and embedded in the inner upper shell 113, the air pump 15 is configured to provide an air source for the atomization assembly 12, so that the atomization assembly 12 atomizes aromatherapy essential oils into mist and diffuses the mist into air.

The base fitting plate 116 of the shell assembly 11 is adapted to be detachably connected to the base mechanism 2.

Please refer to FIGS. 3, 4, 6 and 7, the atomization assembly 12 comprises a main atomization shell 121, a jet tube 122, an atomization head 123, an essential oil tube 124, a mist outlet upper cover assembly 125 and an essential oil bottle 126, wherein the main atomization shell 121 is made of engineering plastic materials and is used as a main structural component of the atomization assembly 12, the jet tube 122 is an engineering plastic short tube with one end narrowed, so as to increase a flow rate during the jet; the atomization head 123 is an engineering plastic pipe fitting, which is used to provide an atomization cavity 1231; the essential oil tube 124 is an engineering plastic hose, which is suitable for absorbing aromatherapy essential oils; and the mist outlet upper cover assembly 125 is composed of one or several plates made of engineering plastic materials, comprising a plate-shaped outer contour and the essential oil bottle 126 is a glass bottle, which is suitable for holding aromatherapy essential oils.

The essential oil bottle 126 is connected to a lower end of the main atomization shell 121 (in the present embodiment, in a manner of threaded connection); inside the main atomization shell 121 forms an air inlet pipe 1211, the air inlet pipe 1211 is integrally formed with the main atomization shell 121, the air inlet pipe 1211 forms an air inlet on a surface of the main atomization shell 121, and an air outlet of the air inlet pipe 1211 is arranged at the lower end of the main atomization shell 121 and faces the essential oil bottle 126, a first mist outlet 1212 is also formed in the main atomization shell 121, and the first mist outlet 1212 communicates with the essential oil bottle 126 and an upper cavity of the main atomization shell 121.

The atomization head 123 is provided with an atomization nozzle 1232 and an essential oil tube connection portion 1233, and the essential oil tube 124 is connected to the essential oil tube connection portion 1233 of the atomization head 123.

An air inlet end of the jet tube 122 is plugged into the air outlet of the air inlet pipe 1211, and an air outlet end of the jet tube 122 and the atomization head 123 are plugged and fixed to each other, so that the air outlet end of the jet tube 122 is aligned with the atomization nozzle 1232 of the atomization head 123, and the essential oil tube 124 is inserted into the essential oil bottle 126; in the present embodiment, an atomization cavity 1231 is formed at where the atomization head 123 locates, meanwhile, the atomization nozzle 1232 is provided at a bottom end of the atomization cavity 1231, the air outlet end of the jet tube 122 is inserted into the atomization cavity 1231 of the atomization head 123 and interference-fitted therewith, so that the air outlet of the jet tube 122 could be aligned with the atomization nozzle 1232.

On the mist outlet cover assembly 125 forms a second mist outlet 1251, the mist outlet cover assembly 125 is embedded and fixed in an upper cavity of the main atomization shell 121; and in the present embodiment, and the two are fixed by snap connection.

The air inlet pipe 1211 of the main atomization shell 121 allows for passage of airflow, when airflow passes through the air inlet pipe 1211 and is ejected from the jet tube 122, near the atomization nozzle 1232 of the atomization head 123 (in the present embodiment, inside the atomization cavity 1231 of the atomization head 123) forms a Venturi effect, so that the atomization head 123 absorbs aromatherapy essential oils from the essential oil bottle 126 through the essential oil tube 124, and the aromatherapy essential oils are atomized into mist at the atomization nozzle 1232 of the atomization head 123, and the mist passes through the first mist outlet 1212 of the main atomization shell 121 and the second mist outlet 1251 of the mist outlet upper cover assembly 125 in sequence and is diffused into air.

Further, inside the mist outlet upper cover assembly 125 is provided a porous plate 1252, in the present embodiment, the porous plate 1252 is fastened into the mist outlet cover assembly 125, through densely distributed holes on the porous plate 1252, the mist passes and gets to the second mist outlet 1251, and excess mist will be liquefied into aromatherapy essential oils on surfaces of the porous plate 1252 and flow back the essential oil bottle 126, thereby avoiding waste of aromatherapy essential oils.

Further, the inner upper shell 113 is provided with an air inlet interface 1131, the air inlet interface 1131 is integrally formed with the inner upper shell 113, an air outlet of the air pump 15 is communicated to the air inlet interface 1131 of the inner upper shall 113 so as to enable the air pump 15 to output airflow to the inner upper shell 113; when the atomization assembly 12 is connected and embedded in the inner upper shell 113, the inner upper shell 113 is sealed, in the present embodiment, outside the main atomization shell 121 of the atomization assembly 12 is sleeved a sealing ring, when the atomization assembly 12 is embedded in the inner upper shell 113, the atomization assembly 12 is detachably fixed by frictional fit between the sealing ring and inner walls of the inner upper shell 113, and the sealing ring cooperates with the inner walls of the inner upper shell 113 to seal the inner upper shell 113; when the air pump 15 runs, airflow is poured into sealed inner upper shell 113 from the air inlet interface 1131, and the airflow sealed in the inner upper shell 113 is forced to pass through the air inlet on the surface of the main atomization shell 121 and enters into the air inlet pipe 1211, thereby providing airflow for the air inlet pipe 1211 of the atomization assembly 12.

Further, inside the inner upper shell 113 is provided a guide plate 117 with a notch 1171, wherein the guide plate locates at a bottom portion of the inner upper shell 113 and can cover the air inlet interface 1131, however, airflow entering the inner upper shell 113 from the air inlet interface 1131 can still pass through the notch 1171 of the guide plate 117 and move upward.

When the air pump 15 runs, airflow is poured into the sealed inner upper shell 113 from the air inlet interface 1131, and the airflow sealed in the inner upper shell 113 is forced to pass through the air inlet on the surface of the main atomization shell 121, enter into the air inlet pipe 1211 and be exhausted from the jet tube 122, and near the atomization nozzle 1232 of the atomization head 123 (in the present embodiment, inside the atomization cavity 1231 of the atomization head 123) forms a Venturi effect, so that the atomization head 123 absorbs aromatherapy essential oils from the essential oil bottle 126 through the essential oil tube 124, and the aromatherapy essential oils are atomized into mist at the atomization nozzle 1232 of the atomization head 123, and the mist passes through the first mist outlet 1212 of the main atomization shell 121, the porous plate 1252 and the second mist outlet 1251 of the mist outlet upper cover assembly 125 in sequence and is diffused into air It can be understood that the main circuit board 13 is equipped with buttons for controlling operation of the air pump 15 and the lamp beads 132, and is further equipped with an indicator light for indicating operating status of the air pump 15 and the lamp beads 132 and charging status of the batteries 14. In the present embodiment, both the buttons and the indicator light pass the bottom shell 111.

Please refer to FIGS. 2~5, and 9, the base mechanism 2 comprises a base assembly 21, a support rod assembly 22, and a rotary connection assembly 23 from bottom to top; and the base fitting plate 116 of the shell assembly 11 of the aroma diffuser body mechanism 1 is adapted to be detachably connected to the rotary connection assembly 23 of the base mechanism 2.

Specifically, the base assembly 21 comprises a main base plate 211 and a base power supply assembly 212; the main base plate 211 is a round flat plate made of engineering plastic or metal materials suitable for being placed on a floor; the base power supply assembly 212 comprises a first box body 2121 and a power supply circuit board 2122, the first box body 2121 is a round box body made of engineering plastic or metal materials, which is used to accommodate the power supply circuit board 2122, which is a printed circuit board (PCB), on the first box body 2121 forms a first slot 2125 (which specifically locates at an upper surface of the first box body 2121); the first box body 2121 is fixed on the main base plate 211, the power supply circuit board 2122 is accommodated in the first box body 2121, the power supply circuit board 2122 is respectively equipped with a second charging interface 2123 and power supply rings 2124, wherein the second charging interface 2123 is one of a Type-C interface, a Micro USB interface and a Mini USB interface, which is mounted on the main circuit board 13 in a form of a plug-in, the power supply rings 2124 are conductive sheets covering on a surface of the power supply circuit board 2111, and are divided into positive and negative electrodes; the second charging interface 2123 penetrates the first box body 2121, and the power supply rings 2124 also pass the first slot 2125 of the first box body 2121.

The support rod assembly 22 comprises a support tube body 221, the support tube body 221 comprises a metal tube, ends of the support tube body 221 are embedded with end shells 222, and inside the end shells 222 are accommodated transfer circuit boards 223, the transfer circuit boards 223 are printed circuit boards (PCBs), the transfer circuit boards 223 are equipped with first conductive pillars 2231, the first conductive pillars 2231 are spring conductive pillars which are mounted on the transfer circuit boards 223 in a form of a plug-in, the first conductive pillars 2231 penetrate surfaces of the end shells 222, and transfer circuit boards 223 at the ends of the support tube body 221 are connected through wires;

the rotary connection assembly 23 comprises a second box body 231 and rotary connection circuit boards 232, wherein the second box body 231 is a round box body made of engineering plastic or metal materials, which is used to accommodate the rotary connection circuit boards 232, which are printed circuit boards (PCB), on the second box body 231 forms a second slot 2311 (which specifically locates at a bottom surface of the second box body 231), the rotary connection circuit boards 232 are accommodated in the second box body 231, the rotary connection circuit boards 232 are respectively equipped with second electricity receiving rings 2321 and second conductive pillars 2322, the second receiving rings 232 comprise thin conductive sheets covering a surface of the power supply circuit board 2122, and are divided into positive and negative electrodes, the second conductive pillars 2322 are spring conductive pillars and are mounted on the rotary connection circuit boards 232 in a form of a plug-in, the second conductive pillars 2322 penetrate the second box body 231, the second electricity receiving rings 2321 also pass the second slot 2311 of the second box body 231.

When either end of the support rod assembly 22 is plugged into the first slot 2125 of the base assembly 21 (in the present embodiment, the two are fixed to each other through cooperation of claws and grooves), the first conductive pillars 2231 of the support rod assembly 22 are in contact with the power supply rings 2124 of the base assembly 21.

When either end of the support rod assembly 22 is plugged into the second slot 2311 of the base assembly 23 (in the present embodiment, the two are fixed to each other through cooperation of claws and grooves), the first conductive pillars 2231 of the support rod assembly 22 are in contact with the second electricity receiving rings 2321 of the rotary connection assembly 23;

On the base fitting plate 116 of the shell assembly 11 of the aroma diffuser body mechanism 1 forms a base fitting slot 1161, actually the base fitting slot 1161 is a circular slot, the main circuit board 13 of the aroma diffuser body mechanism 1 is further equipped with first electricity receiving rings 131, the first electricity receiving rings 131 are thin conductive sheets covering a surface of the main circuit board 13 and is divided into positive and negative electrodes, and the first electricity receiving rings 131 penetrate the base fitting slot 116 of the base fitting plate 1161.

When the rotary connection assembly 23 of the base mechanism 2 is inserted into the base fitting slot 1161 of the aroma diffuser body mechanism 1, the second conductive pillars 2322 of the base mechanism 2 are in contact with the first electricity receiving rings 131 of the aroma diffuser body mechanism 1.

Figure 9:
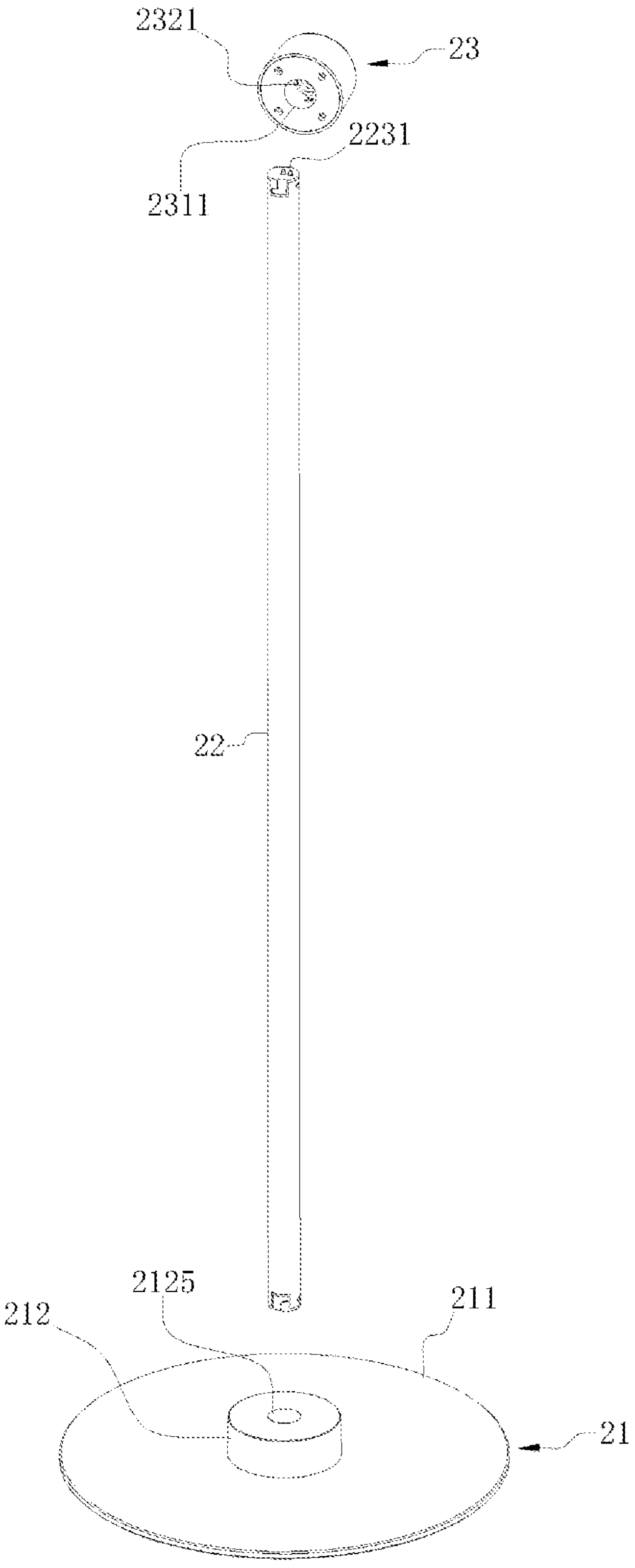
FIG. 9 is a schematic diagram of a separation/combination process of a base mechanism.

Please refer to FIG. 9, it can be understood that the base assembly 21, the support rod assembly 22, and the adapter assembly 23 of the base mechanism 2 can be disassembled from each other for easy storage and transportation. The use of the support rod assembly 22 is not limited by direction, that is, either end of the support rod assembly 22 can be inserted into the first slot 2125 of the base assembly 21 or the second slot 2311 of the adapter assembly 23

Further, inside the base fitting plate 116 of the aroma diffuser body mechanism 1 is provided a first permanent magnet 16 (specifically located at a bottom central position of the base fitting plate 116 and surrounded by the first electricity receiving rings 131); inside the rotary connection assembly 23 of the base mechanism 2 is provided a second permanent magnet 233 (specifically located at a top center of the second box body 231); and when the rotary connection assembly 23 of the base mechanism 2 is inserted into the base fitting slot 1161 of the aroma diffuser body mechanism 1, the first permanent magnet 16 and the second permanent magnet 233 are attracted to each other to realize quick disconnection or connection between the aroma diffuser body mechanism 1 and the base mechanism 2.

Figure 8:
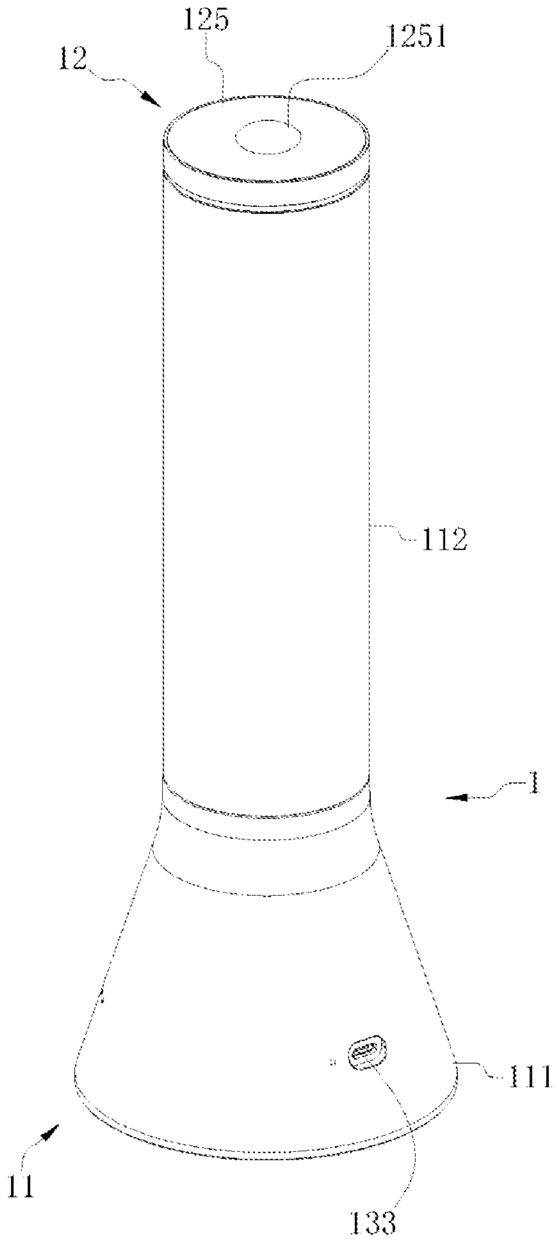
FIG. 8 shows when an aroma diffuser body mechanism is used individually.

Please refer to FIG. 8, in the multi-purpose aroma diffuser of the present embodiment, the aroma diffuser body mechanism 1 can be placed alone (that is, not used in conjunction with the base mechanism 2) on a desktop, a shelf or beside a table for use, at this time, a charging cable of a power adapter can be plugged into the first charging interface 133, supply power to the main circuit board 13 and the air pump 15, and charge the batteries 14; the light guide bracket 115 is relatively close to the desktop, and after the lamp beads 132 on the main circuit board 13 are lit up, a circle of ambient light can be formed on a bottom surface of the aroma diffuser body mechanism 1.

Please refer to FIG. 1 and FIG. 2, in the multi-purpose aroma diffuser of the present embodiment, the aroma diffuser body mechanism 1 can also be used with the base mechanism 2 by placing the base mechanism 2 on a floor and inserting the rotary connection assembly 23 of the base mechanism 2 into the base fitting slot 1161 of the aroma diffuser body mechanism 1, so that the first permanent magnet 16 and the second permanent magnet 233 are attracted to each other to fix the aroma diffuser body mechanism 1, and then the aroma diffuser body mechanism 1 can be supported on the floor, at this time, a charging cable of a power adapter can be plugged into the first charging interface 133 or the second charging interface 2123; and when the charging cable of the power adapter is plugged into the second charging interface 2123, currents pass the second charging interface 2123 of the base assembly 21, the power supply circuit board 2122, the power supply rings 2124, one of the first conductive pillars 2231 and the rotary connection circuit boards 232, and wises of the support rod assembly 2124, another one of the first conductive pillars 2231 and the rotary connection circuit boards 232, the second conductive pillars 2322, and the first electricity receiving rings 131 of the main circuit board 13, thereby powering the main circuit board 13, and the air pump 15 and charging the batteries 14; and the light guide bracket 115 is relatively far away from the ground, and after the lamp beads 13 on the main circuit board 13 are lit up, the aroma diffuser body mechanism 1 can be used as a standing lamp.

In the multi-purpose aroma diffuser of the present embodiment, the aroma diffuser body mechanism 1 is suitable for being placed alone on a table for use, and is also suitable for use in conjunction with the base mechanism 2 and being supported on a floor. In this way, the multi-purpose aroma diffuser in this embodiment is suitable for various settings such as homes, offices, and shops, and lighting/ambient lighting functions are added, which further enhances practical functionality of the multi-purpose aroma diffuser in the present embodiment.

Although some embodiments of the present invention have been illustrated and described, it should be understood by those skilled in the art that various changes, modifications, substitutions, and variations can be made to these embodiments without departing from the principles and spirit of the present invention. The scope of the present invention is defined by the appended claims and their equivalents.

The invention claimed is:

1. A multi-purpose aroma diffuser, comprising an aroma diffuser body mechanism and a base mechanism, wherein the aroma diffuser body mechanism atomizes aromatherapy essential oils into mist and diffuses the mist into air, the base mechanism is suitable for being placed on a floor, the aroma diffuser body mechanism is suitable for being placed on a tabletop, and the aroma diffuser body mechanism is suitable for being detachably connected to the base mechanism, so that the aroma diffuser body mechanism is supported by the base mechanism;

wherein the aroma diffuser body mechanism comprises at least one part which is capable of radiating illumination light/ambient light outwards;

wherein the aroma diffuser body mechanism comprises a shell assembly, an atomization assembly, a main circuit board, batteries and an air pump;

the shell assembly comprises a bottom shell, an outer upper shell connected to upper portions of the bottom shell, an inner upper shell embedded and fixed in the outer upper shell, and a light guide bracket connected below the bottom shell, and a base fitting plate embedded in the light guide bracket;

the main circuit board is fixed in an inner layer of the light guide bracket of the shell assembly, on the main circuit board are respectively provided a first charging interface and lamp beads, the first charging interface penetrates from the bottom shell of the shell assembly, and an emitting surface of the lamp beads faces the light guide bracket of the shell assembly;

both the batteries and the air pump are accommodated and fixed in the shell assembly, and are in electrical connection with the main circuit board respectively;

the atomization assembly is detachably connected and embedded in the inner upper shell, the air pump is configured to provide an air source for the atomization assembly, so that the atomization assembly atomizes aromatherapy essential oils into mist and diffuses the mist into air; and the base fitting plate of the shell assembly is adapted to be detachably connected to the base mechanism.

2. The multi-purpose aroma diffuser according to claim 1, wherein the atomization assembly comprises a main atomization shell, a jet tube, an atomization head, an essential oil tube, a mist outlet upper cover assembly and an essential oil bottle;

the essential bottle is connected to a lower end of the main atomization shell, an air inlet pipe is formed in the main atomization shell, the air inlet pipe forms an air inlet on a surface of the main atomization shell, and an air outlet of the air inlet pipe is arranged at the lower end of the main atomization shell and faces the essential oil bottle, a first mist outlet is also formed in the main atomization shell, and the first mist outlet communicates with the essential oil bottle and an upper cavity of the main atomization shell;

the atomization head is provided with an atomization nozzle and an essential oil tube connection portion, and the essential oil tube is connected to the essential oil tube connection portion of the atomization head;

an air inlet end of the jet tube is plugged into the air outlet of the air inlet pipe, and an air outlet end of the jet tube and the atomization head are plugged and fixed together, so that the air outlet end of the jet tube is aligned with the atomization nozzle of the atomization head, and the essential oil tube is inserted into the essential oil bottle;

on the mist outlet cover assembly forms a second mist outlet, and the mist outlet cover assembly is embedded and fixed in an upper cavity of the main atomization shell; and the air inlet pipe of the main atomization shell allows for passage of airflow, when airflow passes through the air inlet pipe and is ejected from the jet tube, a Venturi effect forms near the atomization nozzle of the atomization head, so that the atomization head absorbs aromatherapy essential oils from the essential oil bottle through the essential oil tube, and the aromatherapy essential oils are atomized into mist at the atomization nozzle of the atomization head, and the mist passes through the first mist outlet of the main atomization shell and the second mist outlet of the mist outlet upper cover assembly in sequence and is diffused into air.

3. The multi-purpose aroma diffuser according to claim 2, wherein inside the mist outlet upper cover assembly is provided a porous plate.

4. The multi-purpose aroma diffuser according to claim 2, wherein the inner upper shell is provided with an air inlet interface and an air outlet of the air pump is communicated to the air inlet interface of the inner upper shall;

when the atomization assembly is connected and embedded in the inner upper shell, the inner upper shell is sealed; and when the air pump runs, airflow is poured into sealed inner upper shell from the air inlet interface, and the airflow sealed in the inner upper shell is forced to pass through the air inlet on the surface of the main atomization shell and enters into the air inlet pipe.

5. The multi-purpose aroma diffuser according to claim 4, wherein inside the inner upper shell is provided a guide plate with a notch.

6. The multi-purpose aroma diffuser according to claim 1, wherein the base mechanism comprises a base assembly, a support rod assembly, and a rotary connection assembly from bottom to top; and the base fitting plate of the shell assembly of the aroma diffuser body mechanism is adapted to be detachably connected to the rotary connection assembly of the base mechanism.

7. The multi-purpose aroma diffuser according to claim 6, wherein the base assembly comprises a main base plate and a base power supply assembly;

the base power supply assembly comprises a first box body and a power supply circuit board, on the first box body forms a first slot, the first box body is fixed on the main base plate, the power supply circuit board is accommodated in the first box body, the power supply circuit board is respectively equipped with a second charging interface and power supply rings, the second charging interface penetrates the first box body, and the power supply rings also pass the first slot; and the support rod assembly comprises a support tube body, ends of the support tube body are embedded with end shells, and inside the end shells are accommodated transfer circuit boards, the transfer circuit boards are equipped with first conductive pillars, the first conductive pillars penetrate surfaces of the end shells, and the transfer circuit boards at the ends of the support tube body are connected through wires;

the rotary connection assembly comprises a second box body and rotary connection circuit boards, on the second box body forms a second slot, the rotary connection circuit boards are accommodated in the second box body, the rotary connection circuit boards are respectively equipped with second electricity receiving rings and second conductive pillars, the second conductive pillars penetrate the second box body, and the second electricity receiving rings also pass the second slot of the second box body;

when either end of the support rod assembly is plugged into the first slot of the base assembly, the first conductive pillars of the support rod assembly are in contact with the power supply rings of the base assembly;

when either end of the support rod assembly is plugged into the second slot of the base assembly, the first conductive pillars of the support rod assembly are in contact with the second electricity receiving rings of the rotary connection assembly;

on the base fitting plate of the aroma diffuser body mechanism forms a base fitting slot, the main circuit board of the aroma diffuser body mechanism is further equipped with first electricity receiving rings, and the first electricity receiving rings pass the base fitting slot of the base fitting plate;

when the rotary connection assembly of the base mechanism is inserted into the base fitting slot of the aroma diffuser body mechanism, the second conductive pillars of the base mechanism are in contact with the first electricity receiving rings of the aroma diffuser body mechanism.

8. The multi-purpose aroma diffuser according to claim 7, wherein inside the base fitting plate of the aroma diffuser body mechanism is provided a first permanent magnet;

inside the rotary connection assembly of the base mechanism is provided a second permanent magnet; and when the rotary connection assembly of the base mechanism is inserted into the base fitting slot of the aroma diffuser body mechanism, the first permanent magnet and the second permanent magnet are attracted to each other.

* * * * *